United States Patent [19]
Shichman et al.

[11] Patent Number: 5,456,400
[45] Date of Patent: Oct. 10, 1995

[54] APPARATUS AND CLIP FOR FASTENING BODY TISSUE

[75] Inventors: Daniel Shichman, Trumbull, Conn.; Boris Zvenyatsky, Bronx, N.Y.

[73] Assignee: United States Surgical Corporation, Norwalk, Conn.

[21] Appl. No.: 52,104

[22] Filed: Apr. 22, 1993

[51] Int. Cl.⁶ .................. A61B 17/064; A61B 17/068
[52] U.S. Cl. .................. 227/176; 227/19; 411/460; 606/219
[58] Field of Search .................. 227/19, 176; 411/460, 411/463; 606/151, 219

[56] References Cited

U.S. PATENT DOCUMENTS

| | | |
|---|---|---|
| 3,638,847 | 1/1972 | Noiles et al. . |
| 3,643,851 | 2/1972 | Green et al. . |
| 3,646,801 | 3/1972 | Caroli .................. 227/19 X |
| 3,650,453 | 3/1972 | Smith, Jr. . |
| 3,662,939 | 5/1972 | Bryan . |
| 3,717,294 | 2/1973 | Green . |
| 3,837,555 | 9/1974 | Green . |
| 3,875,648 | 4/1975 | Bone .................. 227/19 X |
| 4,127,227 | 11/1978 | Green . |
| 4,162,678 | 7/1979 | Fedotov et al. .................. 227/19 X |
| 4,204,623 | 5/1980 | Green . |
| 4,317,451 | 3/1982 | Cerwin et al. . |
| 4,489,875 | 12/1984 | Crawford et al. . |
| 4,493,322 | 1/1985 | Becht .................. 227/19 X |
| 4,522,207 | 6/1985 | Klieman et al. .................. 227/19 X |
| 4,887,756 | 12/1989 | Pachy .................. 227/19 |

Primary Examiner—Rinaldi I. Rada

[57] ABSTRACT

An apparatus for applying a surgical fastener includes a cartridge which holds a plurality of surgical fasteners in an array, a fastener advancing mechanism, and a mechanism for closing the fasteners, which includes an anvil and laterally moving arms to apply lateral force to bend the legs of the distal fastener inwardly to a closed position. The fasteners can be made of a bioabsorbable material.

14 Claims, 8 Drawing Sheets

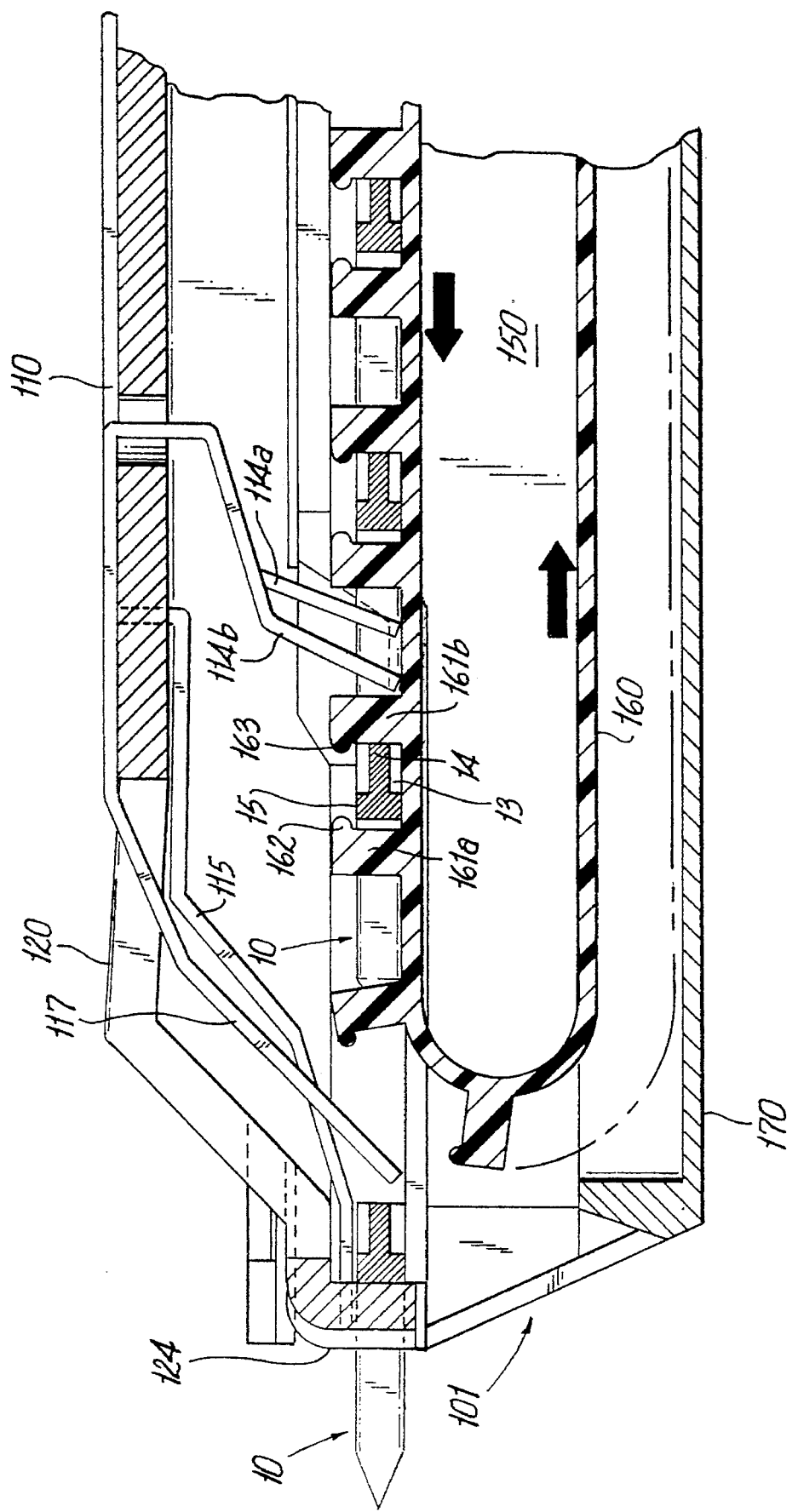

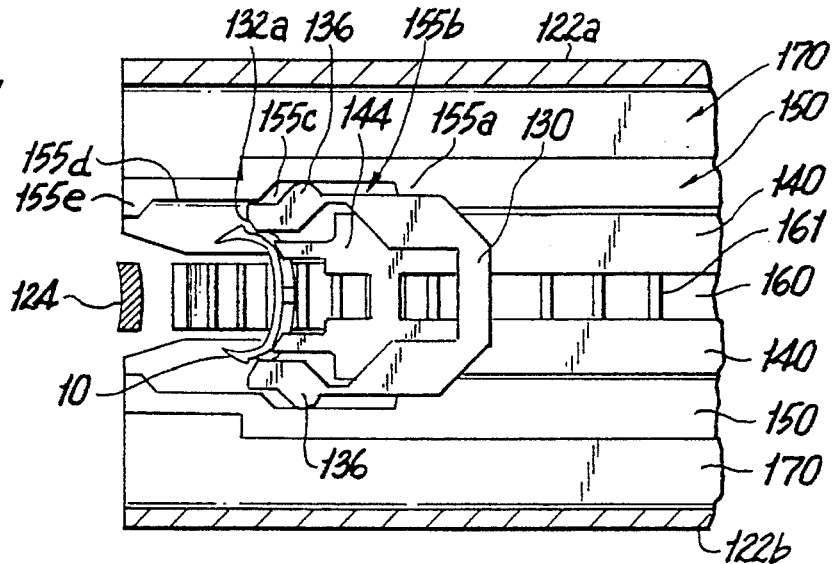
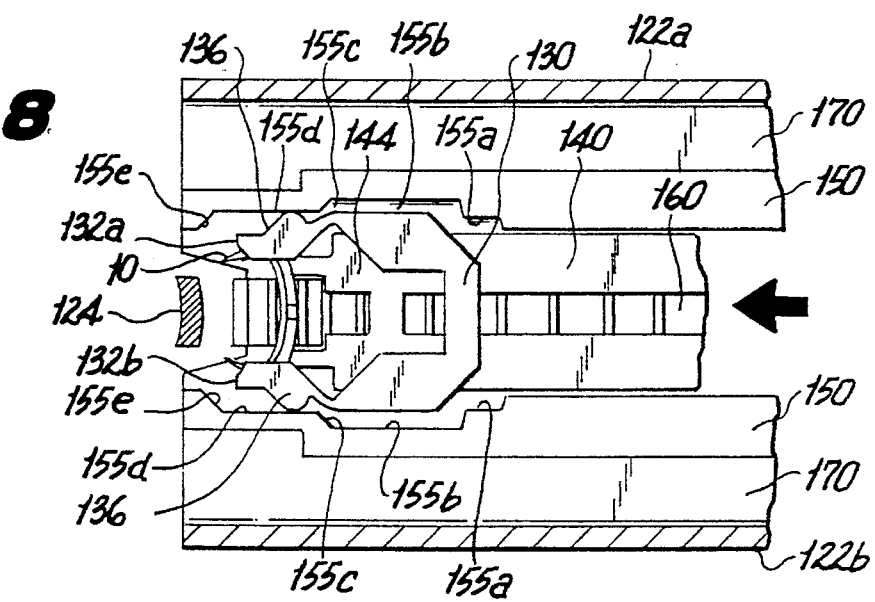
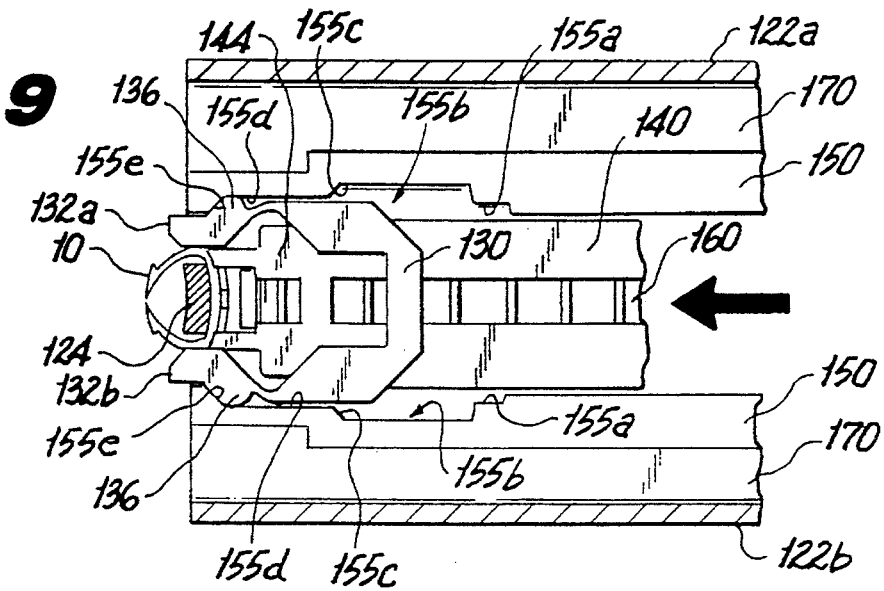

APPARATUS AND CLIP FOR FASTENING BODY TISSUE

BACKGROUND OF THE INVENTION

1. Field of the Invention

The present invention relates to a clip and clip applying apparatus for fastening body tissue. More particularly the invention relates to a surgical clip for fastening skin, fascia, and the like, and to a cartridge for holding and applying said clip.

2. Background of the Art

Skin and fascia fasteners and fastener applying instruments are known in the art and described in various references.

U.S. Pat. No. 4,489,875 to Crawford et al. discloses an instrument for applying staples to skin by bending a staple around an anvil. The staple is a broad based U-shaped metal staple with squared corners. In use, the nose of the instrument is placed against the skin such that the staple straddles the wound or cut to be closed. As the staple is forced against the anvil, the staple bends and the legs penetrate the skin tissue and apply closing pressure across the wound.

U.S. Pat. No. 3,638,847 to Noiles discloses a cartridge for holding a supply of skin fastening staples and advancing them by means of a ratchet mechanism.

U.S. Pat. Nos. 3,717,294 and 3,837,555 to Green disclose a cartridge and powering instrument for stapling skin and fascia. The cartridge includes a belt drive for holding and advancing the staples.

U.S. Pat. Nos. 3,643,851 and 3,662,939 to Green et al. and Bryan, respectively, disclose compressed gas powered staplers for skin and fascia.

U.S. Pat. No. 4,127,227 to Green discloses a cartridge for applying staples to the disunited fascia of a patient. The cartridge is adapted to be inserted into a stapling apparatus which supplies rectilinear thrust to power the cartridge. The cartridge houses a plurality of metal staples mounted on a flexible belt.

U.S. Pat. No. 4,204,623 to Green discloses a manually powered surgical stapler for skin and fascia.

It should be noted that all of the above instruments apply metal staples which are crimped, i.e. bent or formed, around an anvil. While metal staples have proven to be effective in performing their function of fastening tissue, they have the drawback of requiting subsequent removal by a separate operation if they are not intended to be permanently placed. This subsequent removal operation requires an additional, and often painful surgical procedure with a removal instrument.

Also known are instruments for applying bioabsorbable polymeric staples to skin. However, these instruments do not bend or crimp the legs of the staples. Rather, the staple legs remain straight and are typically held in the skin by barbs.

What is needed is an instrument for applying a bendable polymeric skin fastener which can be absorbed into the body without the necessity for a separate removal operation.

SUMMARY OF THE INVENTION

An apparatus is provided herein for applying surgical fasteners. The apparatus comprises a housing, means for holding a plurality of surgical fasteners in an array, the fasteners each having a pair of legs inwardly bendable from an open position to a closed position; means for distally advancing the surgical fasteners; means for sequentially closing the fasteners which includes anvil means for providing a closing surface and laterally moving means for applying force laterally to the legs of a distal one of the fasteners for bending the legs to the closed position.

BRIEF DESCRIPTION OF THE DRAWINGS

FIG. 6 is a sectional elevational view of the distal end of the cartridge.

FIGS. 7, 8 and 9 sequentially illustrate in plan view, the interior of the cartridge in respective stages of clip advancement and closure.

DETAILED DESCRIPTION OF PREFERRED EMBODIMENT(S)

Figure 1:
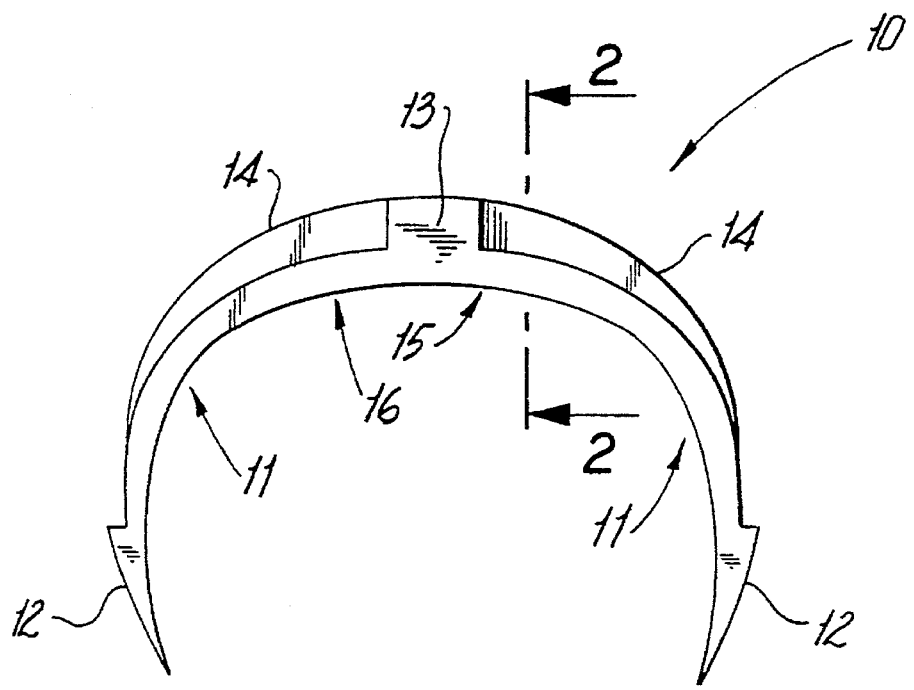
FIG. 1 is a plan view of a surgical clip.
Figure 2:
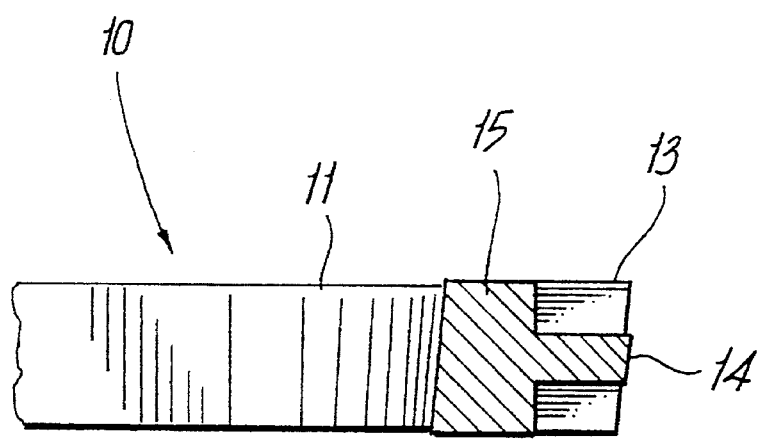
FIG. 2 is a cut away sectional view of the surgical clip.

Referring to FIGS. 1 and 2, a surgical fastener, clip 10, is shown. Clip 10 is intended for use in fastening skin, fascia and the like and may be fabricated not only from metal but also from resinous material. Particularly suitable as material of construction are bioabsorbable polymeric materials such as homopolymers and copolymers of glycolide, lactide, caprolactone, 1,4-dioxanone, trimethylene carbonate and mixtures thereof. Clip 10 is sufficiently flexible and resilient such that its legs may be bent by the clip applier. When the clip is inserted into body tissue, the resilience of the legs provides a biasing force to maintain the gripping action of clip barbs on the body tissue.

More particularly, clip 10 includes a body portion comprising a generally C-shaped span 16 having a back portion 15, leg portions 11 and a backward extending projection 13. A central rib 14 extends backward along the length of the span 16. The clip 10 also possesses at least one barb 12 on the end of each leg portion 11 and extending outwardly therefrom.

Figure 3:
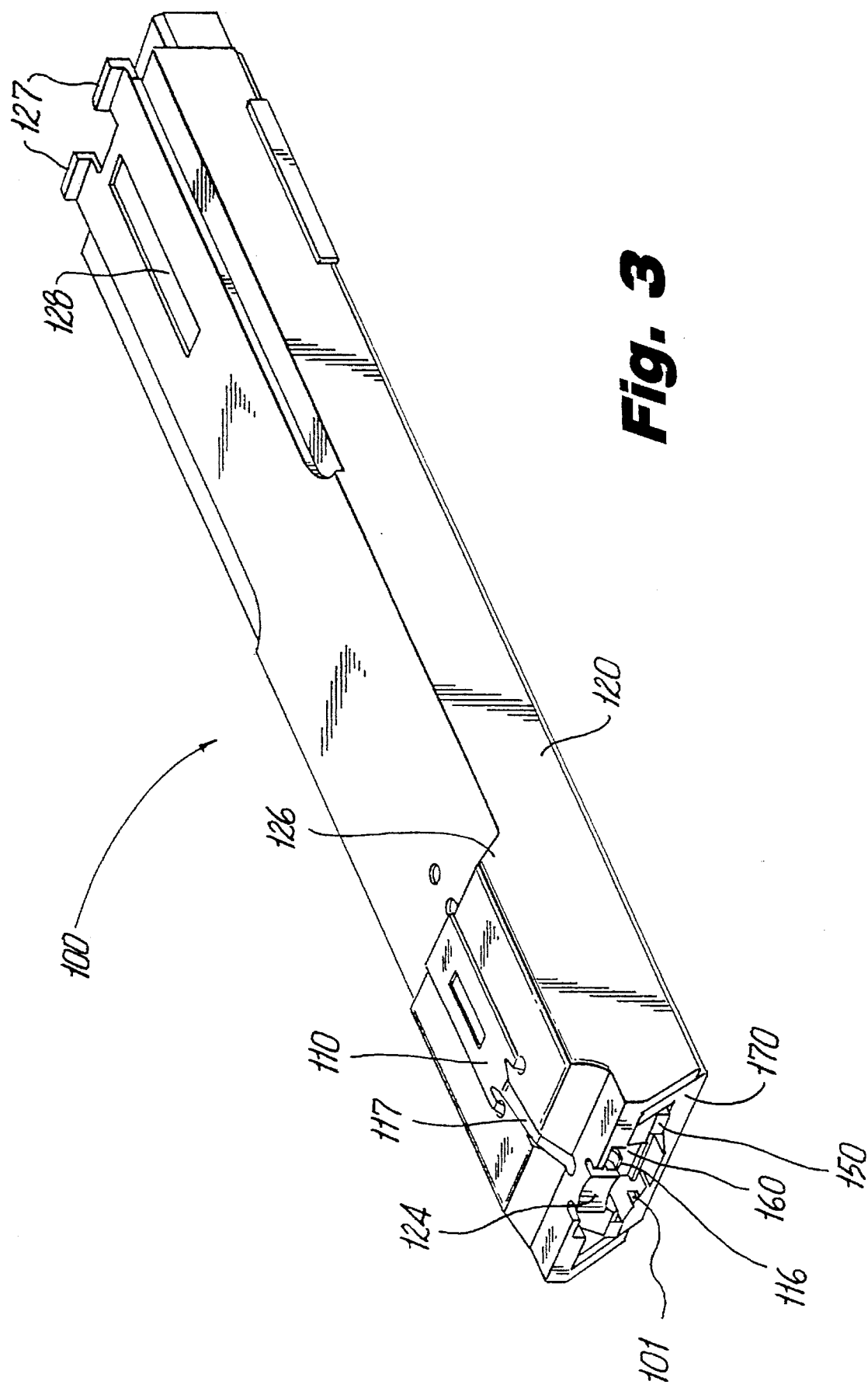
FIG. 3 is a perspective view of the cartridge of the present invention.
Figure 4:
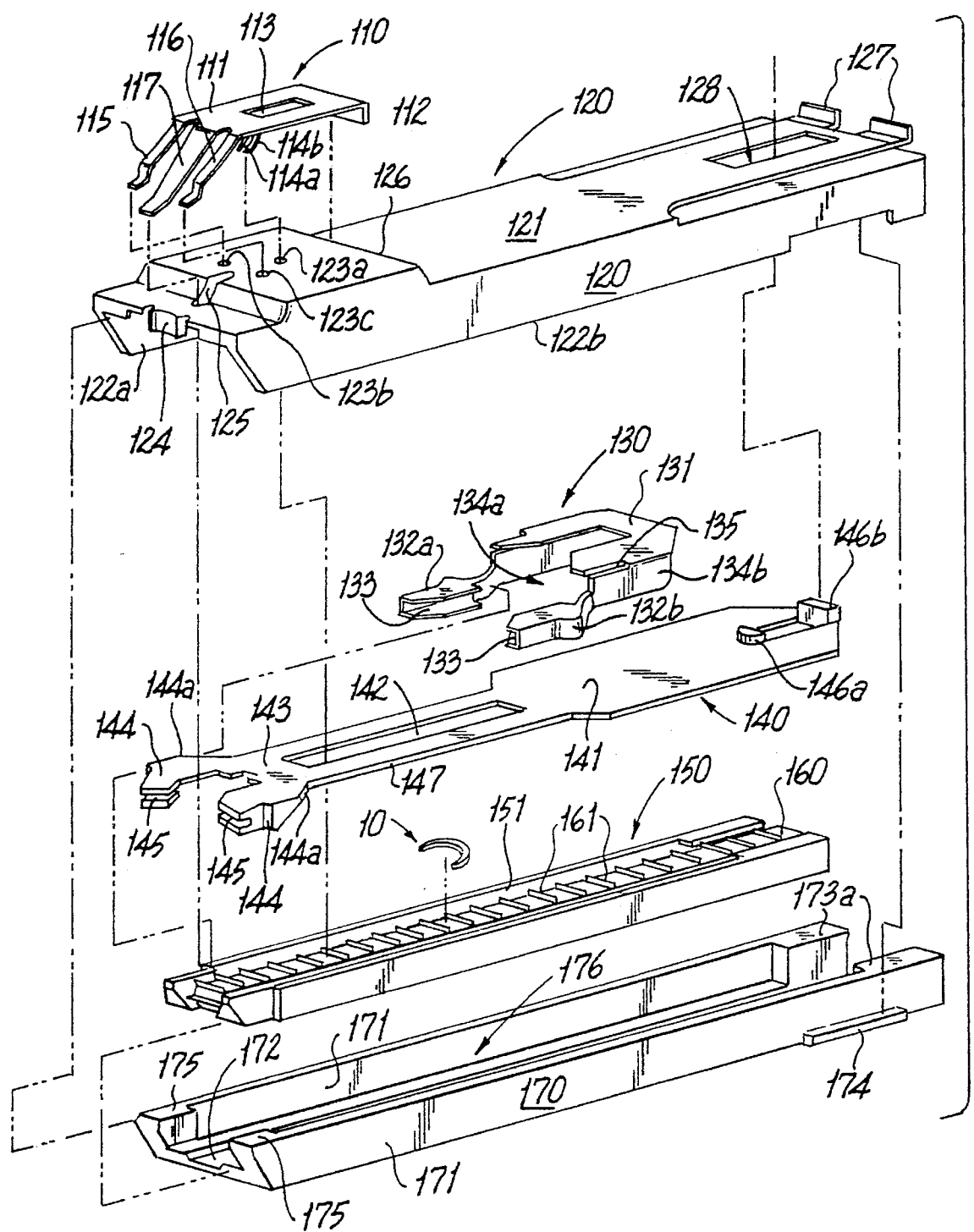
FIG. 4 is an exploded perspective view of the cartridge of the present invention.

Referring to FIGS. 3 and 4, a cartridge for holding and applying clip 10 is shown in assembled and exploded perspective views, respectively.

Ejector clip 110 includes a body plate 111 having a rectangular aperture 113. A rear flap portion 112 is formed by a bend at the proximal end of the body plate 111. Center spring 117, the fight ejector spring 115 and left ejector spring 116 are attached to the distal end of the body plate 111, preferably as integral parts thereof, and bend downwardly therefrom. The center spring 117 facilitates the proper positioning of clip 10 during the clip closing process. Ejector springs 115 and 116 eject the clip from the cartridge through distal opening 101 by pushing the clip down and around the anvil 124, as explained below. Right and left indexing springs 114a and 114b, respectively, depend from the body plate 111 at the distal end of aperture 113.

The upper body 120 is preferably of integral single piece construction and includes a top plate 121 and right and left side portions 122a and 122b, respectively, depending from the top plate 121. An upper projection 126 is located in proximity to the distal end of the upper body 120. Aperture 123a is located on upper projection 126 and is for receiving the indexing springs 114a and 114b of the ejector clip. Apertures 123b and 123c are also located on the upper projection 126 and are for receiving fight and left ejector springs 115 and 116, respectively. Aperture 125 located on the upper projection 126 is for receiving the center spring 117 of the ejector clip. The upper body 120 also includes an anvil 124 located at the distal end thereof.

Figure 5:
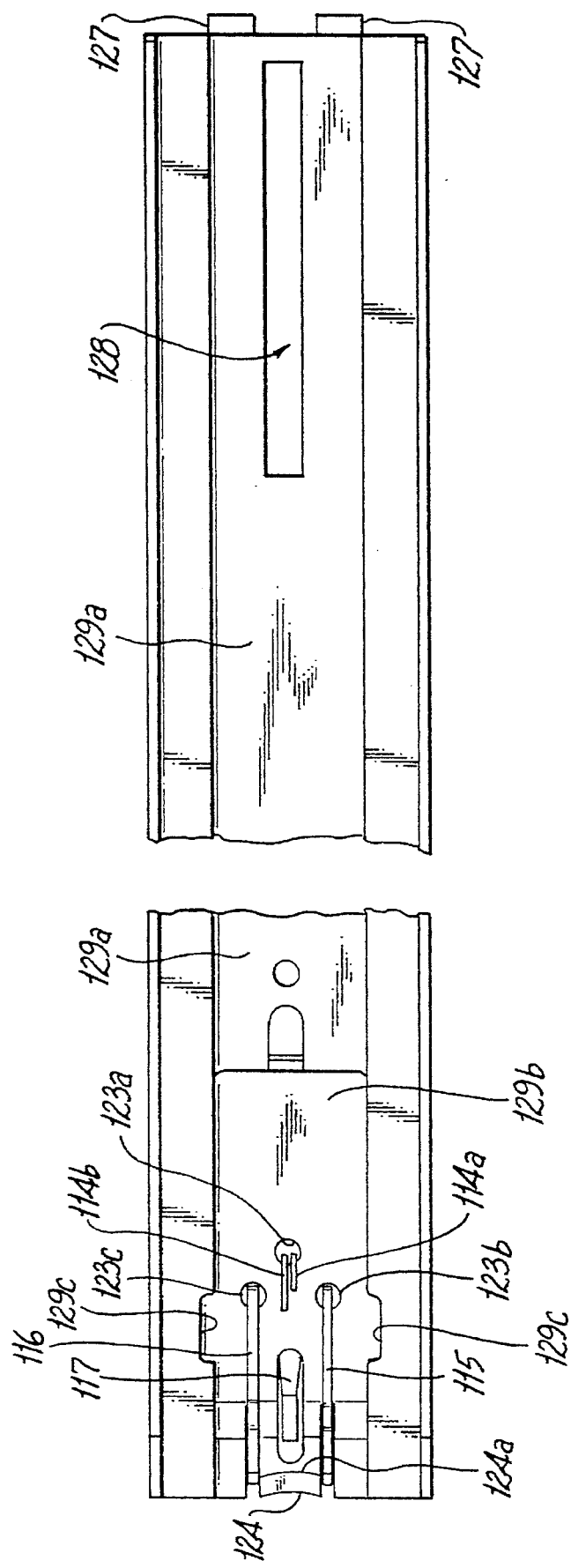
FIG. 5 is a plan view of the upper body.

Referring now to FIG. 5, the underside of the upper body 120 is shown wherein elongated notch 129a extends longitudinally along the inner surface of upper body 120. At the distal end thereof a deeper notch 129b forms a chamber with side niches 129c. Anvil 124 possesses a proximal surface 124a against which the inner surface of back portion 15 of the fastener is pushed for closing of the fastener.

Referring again to FIG. 4, rear flaps 127 extend rearward and upward of the proximal end of the upper body. An elongated slot 128 is located in proximity of the rear portion of the top plate 121. The upper body 120 is integrally fabricated preferably from stainless steel.

Resilient guide clip 130 is preferably of single piece construction and includes a top plate 131, right and left guide springs 132a and 132b, respectively, each guide spring having a notch 133. The guide springs are respectively located on arms 134a and 134b extending distally from the guide clip 130. Notches 135 are located along the respective comer bends formed by the meeting of the arms 134a and 134b and the top plate 131. The guide clip 130 is preferably fabricated from a resilient metal and is fixedly attached, for example by spot welding, to a pusher member 140.

Pusher member 140 is for individually advancing clips 10 through the cartridge and includes a proximal or rear portion 14 1, a relatively narrow middle portion 147 and a forward or distal portion 143. The rear portion 141 includes rear upright projections 146a and 146b, which are slidably disposed in slot 128 of the upper body for receiving an actuating force from the actuating portion of the apparatus. Central portion 147 includes an elongated slot 142 extending longitudinally thereon. Pusher arms 144 extend distally from the front portion 143, each pusher arm 144 including an arm slot 145 for engaging the rib 14 of the clip 10. The proximal side 144a of each arm is inclined so as to permit the arms to ride up and over the next clip in line to be advanced when the pusher member 140 is pulled back in the proximal direction.

Belt 160 is an elongated flexible strip, preferably of polymeric material, which includes upright projections 161 for positioning and carrying forward a line of clips. Belt 160 is located on track 150 which includes a longitudinal recessed portion 151 extending along both the top and bottom sides of the track. The belt 160 is wrapped around track 150 along the longitudinal recessed portion 151 and is slidably movable along the track so as to carry forward the clips 10.

Lower body 170 includes an elongated central portion 176 for receiving and holding track 150. The elongated central portion is defined by projections 173a at the proximal end of the lower body, upward projecting sides 171, and distal projections 175 extending inwardly from sides 171 at the distal end of the lower body. A central indentation 172 extends longitudinally along the length of the lower body.

Projections 174 extend laterally outward from the lower body in proximity to the proximal end thereof.

Referring to FIG. 6, a sectional elevational view of cartridge 100 is shown without pusher member 140 or guide clip 130. The operations of the pusher member 140 and the guide clip 130 are discussed below in connection with FIGS. 7 to 9. The pusher member 140 is initially positioned behind the forwardmost clip 10 in the belt 160. The clips 10 are aligned longitudinally in a single row with each clip being held in between two uprights 161 of the belt 160. Preferably the uprights are shaped such that the upright forward of clip 10, i.e., upright 161a, has a proximal or rearward facing projection 162 at the top of the upright, and the upright distal to the clip 10, i.e. upright 161b, has a distal or forward facing projection 163 at the top of the upright. The two facing projections 162 and 163 help to maintain the clip in position on the belt by forming a narrow neck to prevent passage therethrough of the clip 10.

The clip 10 is advanced by the pusher member 140 until it reaches the anvil 124. Indexing springs 114a and 114b permit distal movement of the belt 160 to advance the clips, but prevent backward movement. The two indexing springs 114a and 114b are spaced longitudinally apart to ensure that at least one indexing spring lodges between the uprights 161 to prevent back movement.

When the clip 10 is advanced to the anvil 124, the guide springs 132 close the clip, as explained below, and the pusher 140 is then withdrawn rearward for positioning behind the next clip. The sloped rear portion 144a of the arms 144 enable the arms to ride up and over the next clip in line.

When the pusher member 140 is disengaged from the clip 10, the ejector springs 115 and 116 press down on the clip 10 and allow it to be withdrawn via distal opening 101 in the cartridge, as seen in FIG. 3. The forward spring 117 prevents back movement of clip 10 once the clip has been advanced to the anvil 124.

Referring now to FIGS. 7, 8 and 9, a plan view of the interior of the cartridge is shown. The right and left guide springs 132a and 132b each have a camming projection 136 positioning outwardly therefrom. The surface of the track member 150 includes camming walls for causing lateral movement of the guide springs 132a and 132b when the guide clip is moved longitudinally. As can be seen in FIGS. 7, 8 and 9, the surface of track member 150 includes a distal chamber section formed by walls 155a, 155b, 155c, 155d and 155e. Wall 155a extends parallel to the longitudinal orientation of the track and serves as a guide for positioning the arms 134 of the guide clip when the guide clip 130 and pusher member 140 are in their most proximal position. Walls 155b define a wider portion of the distal chamber region and are contacted by the camming projections 136. The rib 14 of clip 10 is engaged within slots 145 of arms 144 of the pusher member 140 and the slots 135 of the guide clip 130.

When the pusher member 140 and guide clip 130 are advanced, the camming projections 136 are advanced and contact surfaces 155c which are inclined with respect to the longitudinal orientation of the track and, therefore, urge the guide springs 132a and 132b inwardly as the guide clip 130 is advanced. This, in turn, causes the guide springs 132a and 132b to at least partially close the surgical fastening clip 10 by crimping legs 11 toward each other.

As shown in FIG. 8, the guide clip 130 is advanced to a second stepped region defined by walls 155d which has a narrower width than that defined by walls 155b. As the guide clip 130 is further advanced, the camming projections 136 slide along walls 155d until they reach camming surfaces 155e, which further urge the guide springs 132a and 132b inward for final and complete closure of the arms 11 of the surgical clip 10 around anvil 124, as shown in FIG. 9.

Figure 10:
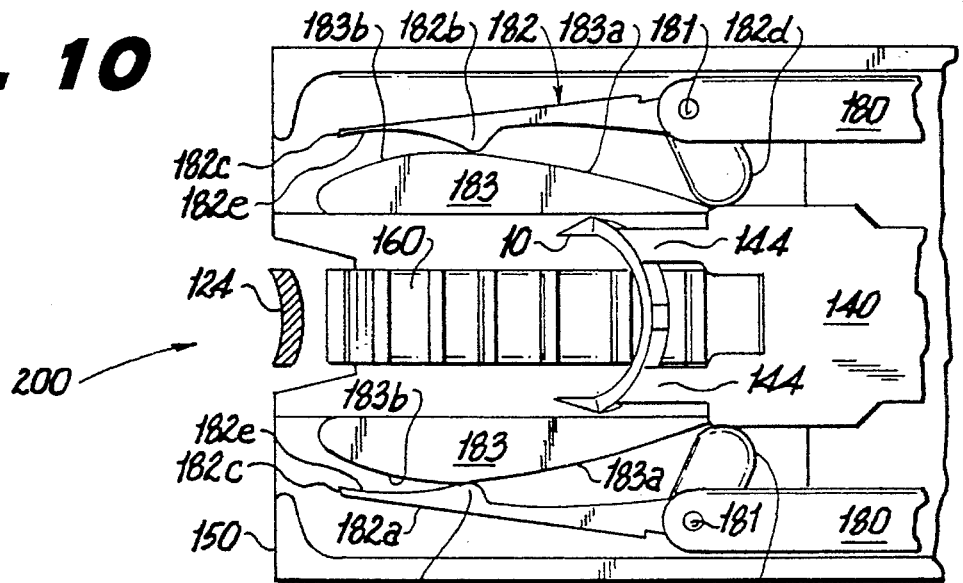
FIGS. 10, 11 and 12 sequentially illustrate an alternative embodiment of the present invention employing pre-piercers in respective stages of clip advancement.
Figure 11:
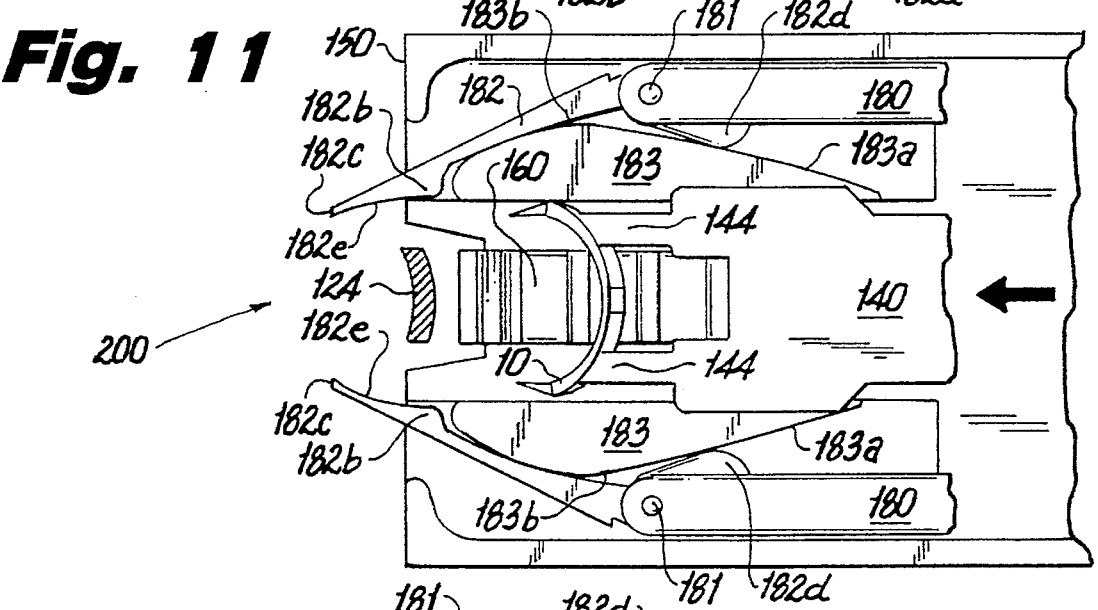
Figure 12:
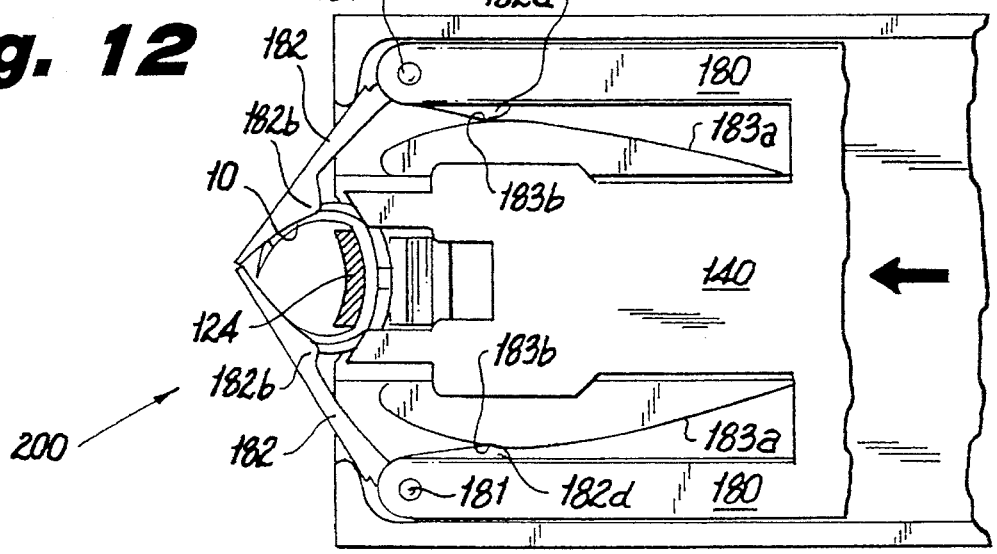

Referring now to FIGS. 10, 11 and 12, an alternative embodiment 200 of the present invention is shown which includes pre-piercers, i.e., means to create a perforation in the skin or body tissue to facilitate entry thereinto by the clip.

In this embodiment, the pusher 140 includes a distal projecting arm 180 on each lateral side. A pre-piercer 182 is pivotally attached to each of the arms 180 at pivot point 181. Each pre-piercer 182 includes an elongated member 182a terminating in a relatively sharp tissue penetrating distal point 182c. Pre-piercers each include a proximal camming projection 182d, a distal camming projection 182b and an arcuate distal surface 182e for contacting the outer edge of the clip 10. Unlike the previously described embodiment 100, alternative embodiment 200 does not include a resilient guide clip 130.

The track member 150 of the alternative embodiment includes interior projections 183 which have arcuate camming surfaces 183a. Initially, both distal and proximal camming projections 182b and 182d, respectively, are in contact with the camming surface 183a, as shown in FIG. 10.

Referring to FIG. 11, when the pusher 140 advances clip 10, camming projections 182d moves forward in sliding contact with arcuate surface 183a. The camming surface 182d curves away from the central longitudinal axis until it reaches a maximum deviation from the central axis at point 183b. Thus, as projection 182d cams along the surface 183a, the pre-piercer 182 is pivoted around pivot point 181 so as to bring the distal piercing point 182c closer to the central longitudinal axis. The distal and pivotal motion of the pre-piercer 182 is illustrated progressively in FIGS. 10 to 12.

When the pre-piercer 182 has advanced to the position shown in FIG. 11, the distal points 182c project through aperture 101 and beyond the distal end of the apparatus so as to penetrate body tissue (not shown) to create punctures for clip entry.

FIG. 12 shows the final stage of pusher advancement. The clip 10 is pushed up to anvil 124 and the pre-piercers 182 are pivoted around such that arcuate distal surfaces 182e of the pre-piercers 182 contact the outer edge of clip 10 to support the clip 10 and to facilitate its closing. The barbed tips 12 of legs 11 of the clip penetrate the body tissue by entering the tissue through the punctures in the skin created by the pre-piercers 182 because it is easier for a clip to enter skin through a pre-pierced puncture, clips used with pre-piercers need not be as strong as clips which are required to create their own punctures. Hence, pre-piercers permit the use of clips that are thinner or smaller, which cause relatively less trauma to the body tissue than larger and thicker clips.

Figure 13:
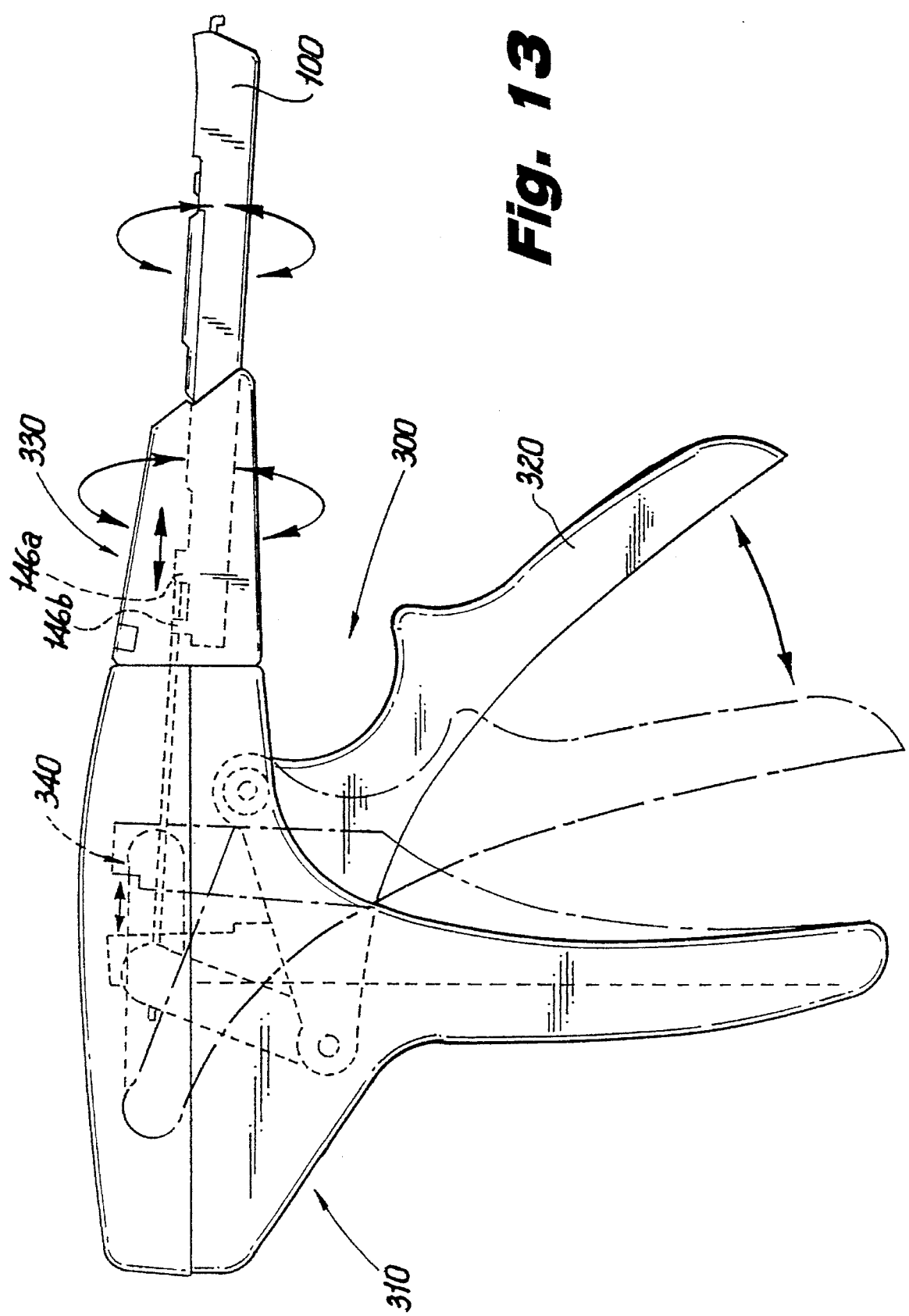
FIG. 13 illustrates an apparatus for applying surgical clips.

The cartridges 100 and 200 described herein may be employed in apparatus such as, for example, the surgical stapling instruments of U.S. Pat. Nos. 4,204,623, herein incorporated by reference in its entirety, and may be adapted to be replaceable, i.e. such that a spent cartridge may be removed from the apparatus and replaced with a fresh one. The apparatus includes means responsive to a user applied force (e.g., a trigger and drive means) to actuate the cartridge for advancing and applying the surgical clips to body tissue. More particularly, an apparatus suitable for receiving and actuating cartridge 100 (or 200) is shown in FIG. 13 wherein surgical stapling apparatus 300 includes a body portion 310 having a rotatable nose portion 330 for receiving and holding cartridge 100. Trigger 320 is pivotally mounted to the body 310 and is linked to drive system 340 which, in turn, engages upright projections 146a and 146b of pusher 140 to actuate cartridge 100 for applying a clip.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A cartridge for use in an apparatus for applying surgical fasteners, which comprises:

a) a housing, and a plurality of surgical fasteners contained therein;

b) a belt for holding the surgical fasteners in an array, said fasteners fabricated from a bioabsorbable synthetic polymer and each having a pair of legs adapted to be inwardly bendable from an open position to a closed position;

c) advancing means for distally advancing said surgical fasteners in a longitudinal direction;

d) means for sequentially closing said fasteners, which includes:

i) anvil means for providing a closing surface; and ii) closing means movable in a direction lateral to said longitudinal direction for applying force laterally to said legs of a distal one of said fasteners for bending said legs to said closed position, wherein said closing means comprises a guide clip mounted to said fastener advancing means and longitudinally movable within said housing, said guide clip having a pair of resilient arm members.

2. The cartridge of claim 1, wherein the bioabsorbable polymer is selected from the group consisting of homopolymers and copolymers of glycolide, lactide, caprolactone, 1,4-dioxanone, trimethylene carbonate and mixtures thereof.

3. The cartridge of claim 1, wherein each fastener is generally C-shaped.

4. The cartridge of claim 1, wherein each said fastener possesses at least one barb.

5. The cartridge of claim 1, wherein said fastener advancing means comprises a pusher bar with a distal fastener engaging means for releasably engaging a surgical fastener.

6. The cartridge of claim 5, wherein said fastener engaging means includes at least one slot.

7. The cartridge of claim 6, wherein each said fastener includes at least one rib for engaging said slot of said fastener engaging means.

8. The cartridge of claim 1, wherein said resilient arm members each comprise an outer camming surface for camming against a corresponding camming surface in the housing, and an inner slot means for engaging the outer portion of a respective one of the surgical fastener legs.

9. A cartridge for use in an apparatus for applying surgical fasteners, which comprises:

a) a housing having a distal end and a plurality of surgical fasteners contained therein;

b) means for holding the surgical fasteners in an array, said fasteners being fabricated from a bioabsorbable synthetic polymer and each having a pair of legs adapted to be inwardly bendable from an open position to a closed position, and resiliently biased to said open position, said legs each having a barbed tissue piercing tip c) advancing means for distally advancing said surgical fasteners in a longitudinal direction;

d) means for sequentially closing said fasteners, which includes:
   i) an anvil means for providing a closing surface, and
   ii) movable closing means for applying force in a direction lateral to said longitudinal direction to said legs of a distal one of said fasteners for bending said legs to said closed position;

e) means mounted to said movable closing means for pre-piercing body tissue to facilitate entry into the body tissue of the tips of the surgical fastener.

10. The cartridge of claim 9, wherein said movable closing means comprises two elongated members pivotally attached to a distal end portion of said fastener advancing means, wherein said elongated members each have an inner side surface for contacting and holding said surgical fastener, and a camming surface for camming against a corresponding camming surface of the housing, said elongated members being movable toward each other upon distal advancement of said fastener advancing means for urging closed said surgical fastener held therebetween.

11. The cartridge of claim 10 wherein said pre-piercing means comprises a distally extending portion on each of said two elongated members which includes a tissue piercing distal tip.

12. A surgical clip, comprising:
   a generally arcuate C-shaped body fabricated front synthetic bioabsorbable polymeric material and having first and second legs each leg having a barbed distal tip, a back portion, and at least one elongated rib extending along a proximal outer surface of a portion of each of said legs, said body being resiliently deformable, said legs being movable between an open configuration wherein they are relatively wider apart, and a closed position wherein they are relatively closer to each other.

13. An apparatus for applying a surgical fastener comprising:
   A) a cartridge which includes
      i) a housing, and a plurality of surgical fasteners contained therein;
      ii) a belt for holding the surgical fasteners in an array, said fasteners each having a pair of legs inwardly bendable from an open position to a closed position;
      iii) means for distally advancing said surgical fasteners in a longitudinal direction;
      iv) means for sequentially closing said fasteners, which includes:
         a) anvil means for providing a closing surface, and
         b) means movable in a direction lateral to said longitudinal direction for applying force laterally to said legs of a distal one of said fasteners for bending said legs to said closed position,
   B) actuation means responsive to a user applied force to actuate said cartridge, and
   C) a frame for receiving said cartridge and supporting said actuation means.

14. The apparatus of claim 13, wherein said actuation means includes a trigger and drive mechanism.

* * * * *